| United States Patent [19] | [11] Patent Number: 4,897,476 |
| Broom | [45] Date of Patent: Jan. 30, 1990 |

[54] PROCESS FOR PREPARING PENEMS

[75] Inventor: Nigel J. P. Broom, Betchworth, England

[73] Assignee: Beecham Group p.l.c., Brentford, England

[21] Appl. No.: 193,746

[22] Filed: May 12, 1988

[30] Foreign Application Priority Data

May 14, 1987 [GB] United Kingdom ............... 8711391

[51] Int. Cl.$^4$ .................. C07D 499/00; A61K 31/43
[52] U.S. Cl. ................................................. 540/310
[58] Field of Search ................ 540/310; 514/192, 195

[56] References Cited

U.S. PATENT DOCUMENTS 4,438,036 3/1984 Corbett et al. ...................... 540/350
4,774,238 9/1988 Broom et al. ....................... 540/310

FOREIGN PATENT DOCUMENTS 0120613 10/1984 European Pat. Off. .
0154132 9/1985 European Pat. Off. .
0210814 2/1987 European Pat. Off. .
0232966 8/1987 European Pat. Off. .
0441768 12/1987 European Pat. Off. .
0150781 8/1989 European Pat. Off. .

OTHER PUBLICATIONS

Tetra Hedron, vol. 39, pp. 78–82, (1983).

*Primary Examiner*—Nicholas S. Rizzo
*Attorney, Agent, or Firm*—Hopgood, Calimafde, Kalil, Blaustein & Judlowe

[57] ABSTRACT

During the preparation of 6-(substituted methylene)-2-penem compounds (which are known for their anti-bacterial and $\beta$-lactamase inhibitory properties) mixtures of the E-isomer and the Z-isomer may be formed. The Z-isomer is, however generally preferred, and the present invention provides a process whereby the E-isomer may be converted into the Z-isomer by reaction with an aromatic heterocyclic thiol in the presence of a base.

12 Claims, No Drawings

PROCESS FOR PREPARING PENEMS

This invention relates to a novel process for the manufacture of (Z)-6-(substituted methylene)-penems.

European Patent Publication No. EP 0 041 768 A (Beecham; published Dec. 16, 1981) discloses 6-(substituted methylene)-2-penems of the general formula (A):

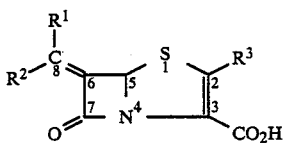

and pharmaceutically acceptable salts and in vivo hydrolysable esters thereof, in which formula each of $R^1$ and $R^2$ denotes hydrogen or an optionally substituted hydrocarbon or heterocyclic group, and $R^3$ denotes hydrogen or an organic group.

(The ring numbering system indicated in formula (A) above is used throughout this specification.)

Those compounds possess antibacterial activity and also inhibit β-lactamases and have a synergistic effect in combination with other β-lactam antibiotics. p European Patent Publication No. EP 0 120 613 A (Beecham; published Oct. 3, 1984) discloses a sub-group of compounds within the general formula (A) which have better activity than other compounds of the general formula (A). That sub-group consists of compounds of the general formula (A) in which:

one of $R^1$ and $R^2$ denotes hydrogen, and p1 the other of $R^1$ and $R^2$ denotes a group of the sub-formula (B):

in which $R^a$ denotes a substituent group;

X denotes an oxygen atom, a sulphur atom or an $=NR^b$ group;

$R^b$ denotes hydrogen, hydrocarbon or a nitrogen-protecting group; and p denotes 0, 1, 2 to 3.

European Patent Publication No. EP 0 150 781 A (Beecham; published Aug. 07, 1985) discloses a further sub-group of compounds of the general formula (A) exhibiting improved β-lactamase inhibitory action and synergistic activity, in which:

one of $R^1$ and $R^2$ denotes hydrogen, and the other of $R^1$ and $R^2$ denotes an unsubstituted or substituted six-membered hetero-aromatic ring bonded through a carbon atom thereof and having from one to three nitrogen atoms as ring hetero-atoms.

European Patent Publication No. EP 0 154 132 A (Beecham; published Sept. 11, 1985) discloses yet further compounds of the general formula (A) exhibiting improved β-lactamase inhibitory action and synergistic activity, in which:

one of $R^1$ and $R^2$ denotes hydrogen, the other of $R^1$ and $R^2$ denotes an unsubstituted or substituted five-membered hetero-aromatic ring bonded through a carbon atom thereof and having one hetero-atom selected from nitrogen, oxygen and sulphur and additionally having from one to three nitrogen atoms.

The compounds of the general formula (A) and their salts and esters may exist in two optically active forms and as racemic mixtures. It is believed that the more active form is that of the general formula (C):

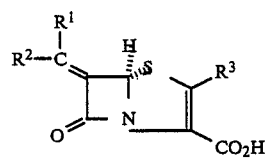

in which $R^1$, $R^2$ and $R^3$ are defined as above.

Furthermore, in general formulae (A) and (C), it is thought to be advantageous that $R^1$ denotes a hydrocarbon or, preferably, heterocyclyl group, and the $R^2$ denotes a hydrogen atom.

One compound specifically described in European Patent publication No. EP 0 154 132 A is the compound of the general formula (C) in which $R^1$ denotes a 1-methyl-1,2,3-triazol-4-yl group and each of $R^2$ and $R^3$ denotes hydrogen, namely:

(5R)  (Z)-6-(1-methyl-1,2,3-triazol-4-yl-methylene) penem-3-carboxylic acid;

as well as its pharmaceutically acceptable salts and in-vivo hydrolysable esters.

European Patent Publication No. EP 0 210 814 A (Beecham; published Feb. 4, 1987) discloses that particular penem in analytically pure form and its salts in crystalline and hydrated forms.

The cited documents describe the preparation of compounds of the general formula (A), or a salt or ester thereof, by eliminating the elements of a compound of the general formula (D):

$$H-X^2 \quad (D)$$

from a penem or penem intermediate (for example, an azetidinone) of the general part-formula (E)

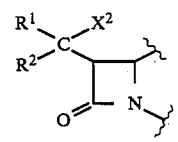

in which $R^1$ and $R^2$ are defined as above, and $X^2$ denotes a hydroxy group or a leaving group, to give a compound of the general part-formula (F):

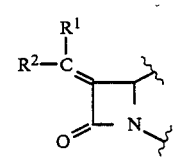

in which $R^1$ and $R^2$ are defined as above, and, if the resulting compound of the general formula (F) is a penem intermediate, converting it into a penem of the general formula (A) or a salt or ester thereof by conventional means.

European Patent Publication No. EP 0 232 966 A (Beecham; published Aug. 19, 1987) discloses novel penems of the general formula (G)

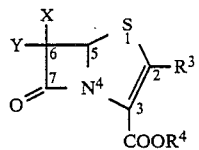

in which
X denotes a halogen atom;
Y denotes a hydrogen atom, a halogen atom, or a moiety of the general formula II

Z denotes a halogen atom, a hydroxy group, a substituted hydroxy group, an $-S(O)_nR^5$ group, or an $-Se(O)_mR^5$ group;
n denotes 0, 1 or 2, preferably 0 or 1;
m denotes 0 or 1;
$R^3$ denotes a hydrogen atom or an organic group;
$R^4$ denotes a hydrogen atom, a carboxy-salt-forming ion,
$R^5$ denotes a hydrogen atom, a hydrocarbon group, or a heterocyclyl group; and
$R^{12}$ denotes a hydrogen atom, an unsubstituted or substituted hydrocarbon group, or an unsubstituted or substituted heterocyclyl group,
and their use in a process for the manufacture of compounds of the general formula (A) wherein one of $R^1$ and $R^2$ denotes hydrogen.

Both of those processes for the manufacture of compounds of the general formula (A) can result in a mixture of the E-isomer (general formulae (A) and (C), $R^1$ denotes hydrogen) and the Z-isomer (general formulae (A) and (C), $R^2$ denotes hydrogen). The Z-isomer is, however, generally preferred to the E-isomer, and the present invention now provides a process whereby the E-isomer may be converted into the Z-isomer.

Accordingly, the present invention now provides a process for the preparation of a compound of the general formula I

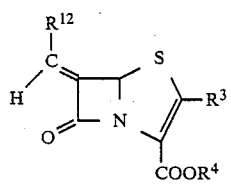

in which
$R^3$ denotes a hydrogen atom or an organic group;
$R^4$ denotes a hydrogen atom, a carboxy-salt-forming ion, or a carboxy-ester-forming group; and
$R^{12}$ denotes an unsubstituted or substituted hydrocarbon group, or an unsubstituted or substituted heterocyclyl group, which process comprises treating a compound of the general formula II

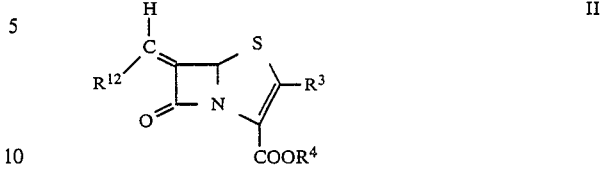

in which $R^3$, $R^4$ and $R^{12}$ are defined as above, with a compound of the general formula III $R^5-SH$     III in which $R^5$ denotes an unsubstituted or substituted aromatic heterocyclyl group,
in the presence of a base.

The term 'hydrocarbon' as used herein includes groups having up to 18 carbon atoms, suitable up to 10 carbon atoms, conveniently up to 6 carbon atoms. Suitable hydrocarbon groups include $(C_{1-6})$alkyl, $(C_{2-6})$alkenyl, $(C_{2-6})$alkynyl, $(C_{3-7})$cycloalkyl, aryl, $(C_{3-7})$cycloalkyl$(C_{1-6})$alkyl, aryl$(C_{1-6})$alkyl, $(C_{1-6})$alkyl$(C_{3-7})$cycloalkyl, and $(C_{1-6})$alkylaryl.

Examples of suitable optional substituents for the above-mentioned hydrocarbon groups include, heterocyclyl, amino, $(C_{1-6})$alkanoylamino, (mono, di, or tri)-$(C_{1-6})$alkylamino, hydroxy, $(C_{1-6})$alkoxy, $(C_{1-6})$alkoxy$(C_{1-6})$alkoxy, aryloxy, mercapto, $(C_{1-6})$alkylthio, heterocyclylthio, arylthio, sulphamoyl, carbamoyl, substituted carbamoyl, amidino, guanidino, nitro, chloro, bromo, fluoro, carboxy and salts and esters thereof, $(C_{1-6})$alkanoyloxy, arylcarbonyloxy, heterocyclylcarbonyloxy, acyl, and acyloxy groups.

Any alkyl group or moiety referred to herein may be straight or branched, unsubstituted or substituted, and may contain, for example, up to 12 carbon atoms, suitably up to 6 carbon atoms. In particular, the alkyl group or moiety may be an unsubstituted or substituted methyl, ethyl, n-propyl, iso-propyl, n-butyl, sec-butyl, isobutyl or tert-butyl group. Examples of suitable optional substituents for any such alkyl group or moiety include the above-listed substituents for hydrocarbon groups, and also the above-listed non-alkyl hydrocarbon groups, including, for example cycloalkyl and aryl groups.

The term 'aryl' as used herein includes phenyl and naphthyl, which may be unsubstituted or substituted by up to five, preferably up to three, groups selected from halogen, $(C_{1-6})$alkyl, phenyl, $(C_{1-6})$alkoxy, halo$(C_{1-6})$alkyl, hydroxy, amino, nitro, carboxy, $(C_{1-6})$alkoxycarbonyl, $(C_{1-6})$alkoxycarbonyl$(C_{1-6})$alkyl, $(C_{1-6})$alkylcarbonyloxy, and $(C_{1-6})$alkylcarbonyl groups, and also the other above-listed substituents for hydrocarbon groups, and the other above-listed non-aryl hydrocarbon groups.

The term 'heterocyclyl' as used herein includes aromatic and non-aromatic, single and fused, rings containing up to four hetero-atoms in each ring selected from oxygen, nitrogen and sulphur, which rings may be unsubstituted or substituted by up to three groups. Suitable substituent groups include the above-mentioned hydrocarbon groups, as well as the optional substituents listed hereinabove as suitable substituents for hydrocarbon groups.

The group $R^{12}$ in the compounds of the general formulae I and II corresponds to the group $R^1$ or $R^2$ in the general formula (A) above, as defined in our various above-mentioned European patent publications (except that it may not be a hydrogen atom).

A hydrocarbon group denoted by $R^{12}$ may suitably be an unsubstituted or substituted $(C_{1-10})$hydrocarbon group, preferably an unsubstituted or substituted $(C_{1-6})$alkyl group or an unsubstituted or substituted phenyl group, and especially an unsubstituted or substituted methyl, ethyl or phenyl group. Such groups are more fully described as the groups $R^1$ and $R^2$ in EP 0 041 768 A.

A heterocyclyl group $R^{12}$ may suitably be an aromatic heterocyclyl group, and in such cases the requirement for aromaticity will, of course, affect the choice of ring size, type and number of hetero-atoms, and type and number of ring substituents in a manner well known to a person skilled in the art (see, for example, M. J. Cook et al, 'Aromaticity of heterocycles', Advances in heterocyclic chemistry, Academic Press, 1974, 17, 255 ff; and A. R. Katritzky and J. M. Lagowski, 'Protopic tautomerism of heteroaromatic compounds', ibid, 1, 311, 339; 2, 1, 27; Supplement 1).

A heterocyclyl group denoted by $R^{12}$ may suitably be an unsubstituted or substituted five-membered or six-membered aromatic heterocyclyl group comprising one or more ring hetero-atoms selected from oxygen, nitrogen and sulphur, the remaining ring atoms being carbon atoms. The heterocyclyl group is advantageously bonded to the remainder of the molecule through a ring carbon atom.

More particularly, a heterocyclyl group $R^{12}$ may be an unsubstituted or substituted five-membered aromatic heterocyclyl group bonded through a carbon atom thereof and having one ring hetero-atom selected from oxygen, nitrogen and sulphur, and optionally additionally having from one to three nitrogen atoms. Such five-membered groups may be groups of the sub-formula (B) given above, as more particularly defined and described in EP 0 120 613 A (wherein $X^1$, $R^a$ and $R^b$ in formula (B) above correspond, respectively, to X, $R^4$ and $R^5$ as defined in EP 0 120 613 A). Alternatively, such five-membered groups may be five-membered hetero-aromatic groups of the type defined and described in EP 0 154 132 A.

Suitable five-membered aromatic heterocyclyl rings $R^{12}$ include furans, thiophenes, pyrroles, pyrazoles, imidazoles, triazoles, tetrazoles, thiazoles, isothiazoles, oxazoles, isoxazoles, thiadiazoles, and oxadiazoles, each of which may be unsubstituted or substituted. (It is to be understood that, where appropriate, all isomeric forms of the above-mentioned aromatic heterocyclyl rings are included).

Particularly suitable five-membered aromatic heterocyclyl rings $R^{12}$ include furans, oxazoles, isoxazoles, pyrazoles, and triazoles.

Examples of individual five-membered aromatic heterocyclyl groups $R^{12}$ include furyl, isothiazolyl, isoxazolyl, methylthiazolyl, methyloxazolyl, dimethyloxazolyl, methyl-1,2,3-thiadiazolyl, methyl-1,2,4-oxadiazolyl, N-methylpyrazolyl, N-methylimidazolyl, N-methyl-1,2,3-triazolyl, N-methyl-1,2,4-triazolyl, and N-methyltetrazolyl groups.

A heterocyclyl group $R^{12}$ may furthermore be an unsubstituted or substituted six-membered aromatic heterocyclyl group bonded through a carbon atom thereof and having from one to three nitrogen atoms as ring hetero-atoms, as more fully defined and described in EP 0 150 781 A.

Suitable six-membered aromatic heterocyclyl rings $R^{12}$ include pyridine, pyrazine, pyrimidine, pyridazine, and triazines, each of which may be unsubstituted or substituted. (It is to be understood that, where appropriate, all isomeric forms of the above-mentioned aromatic heterocyclyl rings are included).

Examples of individual six-membered aromatic heterocyclyl groups $R^{12}$ include 3-pyridyl, 4-pyridyl, methoxypyridyl, pyrazinyl, 4-pyrimidinyl, 3-pyridazinyl, and dimethyltriazinyl groups.

A heterocyclyl group $R^{12}$ may be unsubstituted or may be substituted by one or more substituents, each of which may be carried on a ring carbon atom or a ring nitrogen atom, provided of course that, where appropriate, the aromaticity of the ring is not destroyed.

Examples of suitable substituents which may be present in a heterocyclyl group $R^{12}$ include $(C_{1-6})$alkanoyl, $(C_{1-6})$alkanoyloxy, heterocyclyl, amino, $(C_{1-6})$alkanoylamino, (mono or di)-$(C_{1-6})$alkylamino, hydroxy, $(C_{1-6})$alkoxy, sulpho, mercapto, $(C_{1-6})$alkylthio, $(C_{1-6})$alkylsulphinyl, $(C_{1-6})$alkylsulphonyl, heterocyclylthio, arylthio, sulphamoyl, carbamoyl, amidino, guanidino, nitro, halogen, carboxy, carboxy salts, carboxy esters, arylcarbonyl, and heterocyclylcarbonyl groups, and also unsubstituted or substituted $(C_{1-6})$alkyl, $(C_{2-6})$alkenyl, $(C_{2-6})$alkynyl, aryl, and aryl$(C_{1-6})$alkyl groups.

Examples of suitable optional substituents for the above-mentioned $(C_{1-6})$alkyl, $(C_{2-6})$alkenyl, $(C_{2-6})$alkynyl, aryl and aryl$(C_{1-6})$alkyl substituents include $(C_{1-6})$alkanoyl, $(C_{1-6})$alkanoyloxy, heterocyclyl, amino, $(C_{1-6})$alkanoylamino, (mono or di)-$(C_{1-6})$alkylamino, hydroxy, $(C_{1-6})$alkylsulphinyl, $(C_{1-6})$alkylsulphonyl, heterocyclylthio, arylthio, sulphamoyl, carbamoyl, amidino, guanidino, nitro, halogen, carboxy, carboxy salts, carboxy esters, arylcarbonyl and heterocyclylcarbonyl groups.

When the group $R^{12}$ includes a carboxy salt or carboxy ester substituent, that substituent may be a pharmaceutically acceptable salt or pharmaceutically acceptable ester, but, in the case of intermediates, such a substituent need not be pharmaceutically acceptable.

The group $R^3$ in the general formulae I and II corresponds to the group $R^3$ in the general formula (A) above. $R^3$ denotes a hydrogen atom or an organic group, which may suitably be linked through a sulphur or carbon atom. For example, $R^3$ may denote a hydrogen atom or a group of formula $-R^6$ or $-SR^6$, where $R^6$ denotes an unsubstituted or substituted $(C_{1-10})$hydrocarbon or heterocyclyl group. Preferably, $R^3$ denotes hydrogen, $(C_{1-10})$alkyl or $(C_{1-10})$alkylthio, or substituted $(C_{1-10})$alkyl or substituted $(C_{1-10})$alkylthio, wherein the substituent may be hydroxy, $(C_{1-6})$alkoxy, $(C_{1-6})$alkanoyloxy, halogen, mercapto, $(C_{1-6})$alkylthio, heterocyclylthio, amino, (mono or di)-$(C_{1-6})$alkylamino, $(C_{1-6})$alkanoylamino, carboxy, or $(C_{1-6})$alkoxycarbonyl.

Examples of suitable organic groups $R^3$ include methyl, ethyl, propyl, methylthio, ethylthio, methylsulphinyl, ethylsulphinyl, hydroxymethyl, methoxymethyl, ethoxymethyl, acetoxymethyl, (1 or 2)-acetoxyethyl, aminomethyl, 2-aminoethyl, acetamidomethyl, 2-acetamidoethyl, carboxymethyl, 2-hydroxyethylthio, methoxymethylthio, 2-methoxyethylthio, acetoxymethylthio, 2-aminoethylthio, acetamidomethylthio, 2-acetamidoethylthio, carboxymethylthio, 2-carboxyethylthio, aryl (especially phenyl), arylthio (especially phenylthio), pyridyl, pyrimidyl, isoxazolyl, pyrimidylthio, tetrazolylthio, and pyridylthio groups. In particular, $R^3$ denotes a hydrogen atom.

The —COOR$^4$ substituent in the 3-position of the penems of the general formulae I and II may be a free carboxy substituent, a carboxy salt or a carboxy ester. The salts and esters may be pharmaceutically acceptable but, in the case of intermediate compounds, need not be pharmaceutically acceptable and may suitably be carboxy-protecting groups.

When the compounds of the general formulae I and II include a basic moiety, for example in the groups $R^3$ or $R^{12}$, they may exist in zwitterionic form in conjunction with carboxy group —COOR$^4$, in which case $R^4$ denotes a negative charge.

Pharmaceutically acceptable esters are suitably pharmaceutically acceptable in vivo hydrolysable esters (also referred to as 'metabolisable esters'), namely those esters which hydrolyse in the human body to produce the parent acid or its salt. Such esters may be identified by oral or intravenous administration to a test animal, and subsequent examination of the test animal's body fluids for the presence of the parent acid or a salt thereof.

Suitable in vivo hydrolysable ester groups include those of formulae (a), (b) and (c):

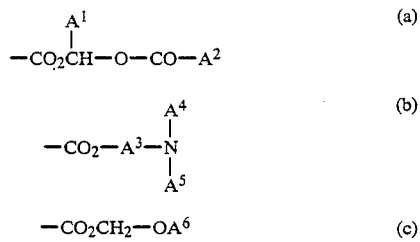

in which
A$^1$ denotes hydrogen, methyl, or phenyl;
A$^2$ denotes (C$_{1-6}$)alkyl, (C$_{1-6}$)alkoxy or phenyl; or
A$^1$ and A$^2$ together denote 1,2-phenylene, which may be unsubstituted or substituted by one or two methoxy groups;
A$^3$ denotes (C$_{1-6}$)alkylene, which may be unsubstituted or substituted by a methyl or ethyl group;
each of A$^4$ and A$^5$ which may be identical or different, denotes (C$_{1-6}$)alkyl; and
A$^6$ denotes (C$_{1-6}$)alkyl.

Examples of suitable in vivo hydrolysable ester groups include acetoxymethyl, pivaloyloxymethyl, α-acetoxyethyl, α-acetoxybenzyl, α-pivaloyloxyethyl, ethoxycarbonyloxymethyl, α-ethoxycarbonyloxyethyl, dimethylaminomethyl, diethylaminomethyl, phthalidyl and dimethoxyphthalidyl groups.

Suitable pharmaceutically acceptable salts of the 3-carboxylic acid group of the compound of formula I include metal salts, e.g. aluminium salts, alkali metal salts (e.g. sodium or potassium salts), alkaline earth metal salts (e.g. calcium or magnesium salts), ammonium salts, and substituted ammonium salts, for example those with lower alkylamines (e.g. triethylamine), hydroxy-lower alkylamines (e.g. 2-hydroxyethylamine, di(2-hydroxyethyl)amine or tri(2-hydroxyethyl)amine), cycloalkylamines (e.g. dicyclohexylamine), or with procaine, and also dibenzylamine, N,N-dibenzylethylenediamine, 1-ephenamine, N-ethylpiperidine, N-benzyl-β-phenethylamine, dehydroabietylamine, N,N'-bishydroabietylethylenediamine, bases of the pyridine type (e.g. pyridine, collidine and quinoline), and other amines which have been or can be used to form salts with penicillins.

A carboxyl-protecting group $R^4$ is suitably a group that can readily be removed at a subsequent process stage.

Examples of suitable carboxy-protecting salt-forming groups $R^4$ include inorganic salts, for example alkali metal atoms (e.g. lithium and sodium) and other metal atoms, and also organic salts, for example tertiary amino groups (e.g. tri-lower-alkylamino, N-ethylpiperadino, and dimethylpiperazino groups). A preferred carboxy-protecting salt-forming group $R^4$ is the triethylamino group.

A carboxy-protecting ester-forming group $R^4$ is advantageously one that can be removed under conventional conditions, such as hydrolysis, hydrogenolysis, or acid cleavage. Examples of suitable carboxy-protecting ester-forming groups $R^4$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, allyl, acetonyl, t-butyl, t-amyl, diphenylmethyl, triphenylmethyl, adamantyl, 2-benzyloxyphenyl, 4-methylthiophenyl, tetrahydrofuran-2-yl, tetrahydropyran-2-yl, pentachlorophenyl, p-toluene-sulphonylethyl, and methoxymethyl groups, and also silyl, stannyl and phosphorus-containing groups, and oxime radicals of formula —N=CHR° in which R° denotes aryl or heterocyclyl, as well as the above-mentioned in vivo hydrolysable ester groups.

When desired, the free carboxyl group may be regenerated from any of the above esters by usual methods appropriate to the particular $R^4$ group, for example, by hydrolysis (which may, for example, be acid-catalysed, base-catalysed, enzymically-catalysed or Lewis-acid-mediated), or by reduction (for example, by hydrogenation).

The compounds of the general formula I may exist in two optically active forms at the 5-position and it is to be understood that the preparation of both such forms as well as racemic mixtures thereof is embraced by the present invention. Advantageously, the compounds are of the formula IA:

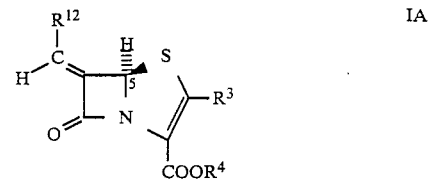

in which $R^3$, $R^4$, and $R^{12}$ are defined as above.

Analogously, the compounds of the general formula II may exist in two optically active forms and the present invention embraces the use of both such forms as well as racemic mixtures thereof. Advantageously the compounds are of the formula IIA:

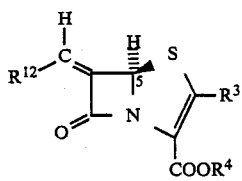

in which $R^3$, $R^4$ and $R^{12}$ are defined as above.

In the process according to the present invention, a (E)-6-(substituted methylene)-penem of the general formula II is treated with an aromatic heterocyclic (or heteroaromatic) thiol of the general formula III in the presence of a base, to give a (Z)-6-(substituted methylene)-penem of the general formula I.

The E-isomer starting material may, if desired, be used in admixture with the Z-isomer, to give a product consisting substantially of the Z-isomer. This may be convenient, for example, because, as mentioned previously, certain preparative processes can result in a mixture of E-isomer and Z-isomer and the entire mixture may then be carried through the process of the invention in order to obtain a product consisting substantially of the Z-isomer, without the need for intermediate separation of the E- and Z-isomers.

The aromatic heterocyclyl group $R^5$ in the aromatic heterocyclic thiol of the general formula III may, for example, be a monocyclic or a bicyclic group and may be unsubstituted or substituted.

In the case of polycyclic (which term, as used herein, includes bicyclic) aromatic heterocyclyl groups $R^5$, either the entire ring system of two or more rings should constitute a single aromatic system, or at least the ring carrying the mercapto substituent should be aromatic. Also in the case of polycylic systems, not all rings of the ring system need be heterocyclic, but at least the ring carrying the mercapto substituent should be heterocyclic. Polycylic ring systems may include a bridgehead nitrogen atom, that is to say, a nitrogen atom common to two or more rings.

The aromatic heterocyclic group $R^5$ may suitably contain up to four hetero-atoms (that is to say, non-carbon atoms) per ring, selected from oxygen, nitrogen and sulphur atoms. Each ring may suitably contain 5 or 6 ring atoms (including carbon atoms and hetero-atoms). The ring size and also the number and type of hetero-atoms must, of course, be consistent with the requirement for aromaticity, in a manner well known to a person skilled in the art (see, for example, the references cited previously).

Preferred aromatic heterocyclic groups $R^5$ are those containing from 1 to 4 nitrogen atoms, especially 1 or 2 nitrogen atoms, as the only hetero-atoms. Also, preferably the aromatic heterocyclic group $R^5$ is monocyclic, in which case it preferably contains 6 ring atoms.

Examples of suitable aromatic heterocyclic groups $R^5$ include unsubstituted and substituted pyridyl, pyrazinyl, pyrimidinyl, pyridazinyl, and benzthiazolyl groups.

Examples of substituents for substituted aromatic heterocyclic groups $R^5$ include the above-mentioned substituents for heterocyclyl groups, although the number and type of substituent must be consistent with the requirement for aromaticity, in a manner well known to a person skilled in the art (see, for example, the references cited previously). Substituents may be present on a ring nitrogen atom or a ring carbon atom. Preferably, however, ring nitrogen atoms are unsubstituted. Preferred substituents are alkyl groups, especially methyl groups. Preferably, the aromatic heterocyclic group $R^5$ is unsubstituted or contains one or two ring substituents.

The aromatic heterocyclic group $R^5$ is bonded to the mercapto group, in the general formula III, through a ring carbon atom, preferably through a ring carbon atom adjacent to a ring hetero-atom.

Examples of suitable aromatic heterocyclic thiols of the general formula III include mercapto-pyridines (for example, 2-mercapto-pyridine), mercapto-pyrimidines (for example, 2-mercapto-pyrimidine), mercapto-dimethyl-pyrimidines (for example, 2-mercapto-4,6-dimethyl-pyrimidine), and mercapto-benzthiazoles (for example, 2-mercapto-benzthiazole).

(Certain aromatic heterocyclic thiols of the general formula III may exist in tautomeric forms. 2-mercapto-pyrimidine, for example, may exist in the following forms:

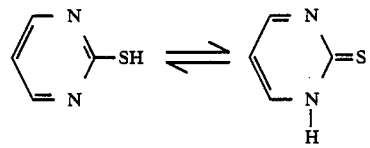

All tautomeric forms of aromatic heterocyclic thiols are included within the scope of the present invention).

The aromatic heterocyclic thiol of the general formula III is suitably used in an amount within the range of from 0.01 to 2 moles per mole of the penem of the general formula II.

The base used in the process according to the invention may be an organic or inorganic base. Suitable inorganic bases include, for example alkali metal carbonates (for example, potassium carbonate). Suitable organic bases include substituted amines, especially tertiary amines, including, for example, N-ethyl-N,N-diisopropylamine and N-benzyl-N,N-dimethylamine.

The base may suitably be present in the reaction mixture in an amount within the range of from 0.01 to 2 moles per mole of the penem of the general formula II. It has been found that in some cases the use of smaller amounts of the base may result in a slower reaction but increased yield, as compared with the use of larger amounts of the same base. The optimum amount of base for any particular reaction conditions and reactants may readily be ascertained by trial experiments.

The reaction may be carried out in an aqueous or organic solvent or diluent, preferably a polar solvent or diluent. Examples of suitable organic solvents or diluents include dimethylformamide, dichloromethane, tetrahydrofuran, and acetonitrile. A mixture of one or more organic solvents/diluents with water, or a mixture of two or more organic solvents/diluents, may be used. Alternatively, the reaction may be carried out under phase transfer conditions.

The solvent or diluent chosen should advantageously be one in which the (E)-penem of the general formula II and the thiol of the general formula III are at least partially soluble.

The solubility of the (E)-penem of the general formula II may in some cases be affected by the choice of the carboxy or substituted carboxy group —COOR⁴. When the group $R^4$ is simply a carboxy-protecting group (as discussed previously) intended for later removal or substitution, it may be convenient to use a group giving improved solubility of the penem in the desired solvent. The optimum choice of carboxy-protecting group and solvent for any particular penem may readily be ascertained by simple solubility experiments.

The duration of the reaction of the (E)-penem of the general formula II with the thiol of the general formula III may vary from about 30 minutes to 2 days or more depending on the choice of thiol, base and solvent, and on the reaction temperature. As discussed previously, a slower reaction can in some cases be advantageous, resulting in an improved yield. The progress of the reaction may in any case readily be monitored by, for example, thin layer chromatography (t.l.c.) or high-performance liquid chromatography (h.p.l.c.). As the β-lactam ring of both the (E)- and (Z)-penems is slowly degraded under the reaction conditions, the reaction is advantageously terminated when the concentration of the (Z)-penem is at its peak.

The process according to the invention may be carried out at a temperature within the range of from −30° to +100° C., advantageously from −10° to +40° C., preferably at from 0° to +25° C., especially at room temperature.

Advantageously the reaction mixture is diluted with a suitable solvent prior to work up to prevent emulsion problems occuring during the extraction procedure. Preferably, the solvent is ethyl acetate and the reaction mixture is diluted threefold.

The desired (Z)-penem of the general formula I may be isolated from the reaction mixture and worked up in conventional manner.

The following examples illustrate the process according to the invention.

EXAMPLE 1

(5R) p-Nitrobenzyl (Z)-6-(1-methyl-1,2,3-triazol-4-ylmethylene)penem-3-carboxylate A solution of the (E)-isomer of the title compound (40 mg, 0.1 mmol) in dimethylformamide (DMF) 4 ml) was treated with 2-mercaptopyrimidine (12 mg, 0.11 mmol) and potassium carbonate (8 mg, 0.12 mmol). After one hour, the reaction mixture was diluted with ethyl acetate, washed well with water and brine, then dried (MgSO₄) and evaporated. The residue was chromatographed on silica eluting with dichloromethane/ethyl acetate mixtures to provide the title compound, 15 mg (37%). This material was identical with an authentic sample.

EXAMPLE 2

(5R) p-Nitrobenzyl (Z)-6-(1-methyl-1,2,3-triazol-4-ylmethylene)penem-3-carboxylate Example 1 was repeated on the same scale using the potassium carbonate in only a catalytic amount. After 16 hours, the reaction mixture was diluted with dichloromethane and then worked-up as previously described to give the title compound, 25 mg (62%).

EXAMPLE 3

(5R) p-Nitrobenzyl (Z)-6-(1-methyl-1,2,3-triazol-4-ylmethylene)penem-3-carboxylate A solution of the (E)-isomer of the title compound (40 mg, 0.1 mmol) in DMF (4ml) was treated with 2-mercaptopyrimidine (12 mg, 0.11 mmol) and diisopropylethylamine (17.4 μl). After one hour, the reaction mixture was worked-up as described in Example 1 to afford the title compound, 17 mg (42%).

EXAMPLE 4

(5R) p-Nitrobenzyl (Z)-6-(1-methyl-1,2,3-triazol-4-ylmethylene)penem-3-carboxylate Example 3 was repeated on the same scale using the diisopropylethylamine in an amount of only 1.74 μl. After 24 hours, the reaction mixture was worked-up as previously described to give the title compound, 22 mg (55%).

EXAMPLE 5

(5R) p-Methoxybenzyl (Z)-6-(1-methyl-1,2,3-triazol-4-ylmethylene)penem-3-carboxylate A solution of the (E)-isomer of the title compound (38 mg, 0.1 mmol) in acetonitrile (4 ml) was treated with diisopropylethylamine (17.4 μl). 2-Mercaptopyrimidine (12 mg, 0.11 mmol) was then added and the mixture stirred for 3 hours. The solvent was removed by evaporation, dichloromethane was added, and the mixture was washed with 5% citric acid solution and brine, then dried (MgSO₄) and evaporated. Chromatography of the residue on silica eluting with ethyl acetate/hexane mixtures provided the title compound, 22 mg (58%). This material was identical with an authentic sample.

EXAMPLE 6

(5R) p-Methoxybenzyl (Z)-6-(1-methyl-1,2,3-triazol-4-ylmethylene)penem-3-carboxylate A solution of 4,6-dimethyl-2-mercaptopyrimidine (14 mg, 0.1 mmol) and the (E)-isomer of the title compound (38 mg, 0.1 mmol) in acetonitrile (4 ml) was treated with diisopropylethylamine (17.4 μl). After 30 minutes, the reaction mixture was worked-up as described in Example 5 to afford the title compound (22 mg).

EXAMPLE 7

(5R) p-Methoxybenzyl (Z)-6-(1-methyl-1,2,3-triazol-4-ylmethylene)penem-3-carboxylate EXAMPLE 6 was repeated on the same scale using N-benzyldimethylamine (15 μl) as the base instead of the diisopropylethylamine. After 30 hours, the reaction mixture was worked-up as previously described to provide the title compound (15 mg).

EXAMPLE 8

(5R) p-Methoxybenzyl (Z)-6-(1-methyl-1,2,3-triazol-4-ylmethylene)penem-3-carboxylate Example 6 was repeated on the same scale using the diisopropylethylamine in an amount of only 1.74 μl. After 3.5 hours, the reaction was worked-up as previously described to afford the title compound (24 mg).

EXAMPLE 9

(5R) p-Methoxybenzyl (Z)-6-(1-methyl-1,2,3-triazol-4-ylmethylene)penem-3carboxylate A solution of the (E)-isomer of the title compound (38 mg) and 2-mercaptopyrimidine (12 mg) in DMF (4 ml) was treated with diisopropylethylamine (17.4 μl). After one hour, the reaction mixture was diluted with ethyl acetate, washed with 5% citric acid solution and brine then dried and evaporated. Chromatography on silica eluting with ethyl acetate/hexane mixture afforded the title compound (15 mg).

EXAMPLE 10

(5R) p-Methoxybenzyl (Z)-6-(1-methyl-1,2,3-triazol-4-ylmethylene)penem-3-carboxylate Example 9 was repeated on the same scale using 2,4,6-collidine (13 μl) as the base instead of the diisopropylethylamine. The progress of the reaction was monitored by t.l.c. (70% v/v ethyl acetate/hexane) and h.p.l.c.. (H.p.l.c. was performed on a Beckman 110B instrument using an Ultrasphere ODS column with pH 5, 0.05M sodium acetate buffer solution containing acetonitrile as eluant at 1.5 ml/min, the compounds being detected by u.v. spectroscopy at λ280 nm. 50% acetonitrile; $R_t$ for E-isomer, 4 min; $R_t$ for Z-isomer, 4.6 min). After 48 hours, h.p.l.c. showed that the title compound (approx. 16 mg) was present in the reaction mixture.

EXAMPLE 11

(5R) p-Methoxybenzyl (Z)-6-(1-methyl-1,2,3-triazol-4-ylmethylene)penem-3-carboxylate Example 9 was repeated on the same scale using 2,6-lutidine (12 μl) as the base instead of the diisopropylethylamine. After 48 hours, h.p.l.c. (see Example 10) showed that the title compound (approx. 5 mg) was present in the reaction mixture.

EXAMPLE 12

(5R) p-Methoxybenzyl (Z)-6-(1-methyl-1,2,3-triazol-4-ylmethylene)penem-3carboxylate A solution of the (E)-isomer of the title compound (38.4 g; 0.1 mol) in acetonitrile (3 liters) was treated with 2-mercaptopyrimidine (11.2 g; 0.1 mol) and diisopropylethylamine (0.174 ml, 0.129 g, 0.01 mol, 0.1 eq.) and stirred at room temperature. After 4 h the concentration of Z-isomer had reached a maximum (HPLC analysis) and ethyl acetate (8 liters) was added. The mixture was extracted with 5% aqueous citric acid (3×2 liters), wash with water (2 liters) and brine (2liters), and the ethyl acetate removed in vacuo. The residue was taken up in dichloromethane (1 liter) and filtered through a plug of silica (40-63 μm) the product being eluted with ethyl acetate (2 liters). The solution was concentrated to ca. 150 ml and the title compound collected by filtration and dried in vacuo, 20.44 g (53.2%).

I claim:

1. A process for the preparation of a compound represented by formula I

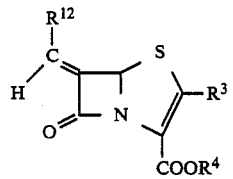

in which $R^3$ denotes a hydrogen atom, $(C_{1-10})$ alkyl, $(C_{1-10})$alkylthio, substituted $(C_{1-10})$alkyl, or substituted $(C_{1-10})$ alkylthio, wherein the substituent may comprise hydroxy, $(C_{1-6})$ alkoxy, $(C_{1-6})$alkanoyloxy, halogen, mercapto, $(C_{1-6})$alkylthio, heterocyclylthio, amino, (mono or di)-$(C_{1-6})$alkylamino, $(C_{1-6})$ alkanoylamino, carboxy, or $(C_{1-6})$alkoxycarbonyl;

$R^4$ denotes a hydrogen atom, a carboxy-salt-forming ion, or a carboxy-ester-forming group; and $R^{12}$ denotes an unsubstituted or substituted $(C_{1-6})$ alkyl group or an unsubstituted or substituted phenyl group where the substituents are chosen from the group consisting of heterocyclyl, amino, $(C_{1-6})$alkanoylamino, (mono, di, or tri)-$(C_{1-6})$alkylamino, hydroxy, $(C_{1-6})$alkoxy, $(C_{1-6})$ alkoxy(C$_{1-6}$)alkoxy, aryloxy, mercapto, $(C_{1-6})$alkylthio, heterocyclylthio, arylthio, sulphamoyl, carbamoyl, substituted carbamoyl, amidino, guanidino, nitro, chloro, bromo, fluoro, carboxy and salts and esters thereof, $(C_{1-6})$alkanoyloxy, arylcarbonyloxy, heterocyclylcarbonyloxy, acyl, acyloxy, cycloalkyl and aryl groups, or denotes an unsubstituted or substituted 5-membered or 6-membered aromatic heterocyclyl group having one or more ring hetero-atoms selected from oxygen, nitrogen or sulfur, the remaining atoms being carbon and the substituent(s) being one or more groups selected from $(C_{1-6})$ alkanoyl, $(C_{1-6})$alkanoyloxy, heterocyclyl, amino, $(C_{1-6})$ alkanoylamino, (mono or di)-$(C_{1-6})$alkylamino, hydroxy, $(C_{1-6})$ alkoxy, sulpho, mercapto, $(C_{1-6})$alkylthio, $(C_{1-6})$alkylsulphinyl, $(C_{1-6})$alkylsulphonyl, heterocyclylthio, arylthio, sulphamoyl, carbamoyl, amidino, guanidino, nitro, halogen, carboxy, carboxy salts, carboxy esters, arylcarbonyl, hetercyclylcarbonyl groups, and unsubstituted or substituted $(C_{1-6})$alkyl, $(C_{2-6})$ alkenyl, $(C_{2-6})$alkynyl, aryl, and aryl$(C_{1-6})$alkyl groups, which process comprises reacting, at a temperature in the range of from −30 to +100° C., a compound represented by formula II

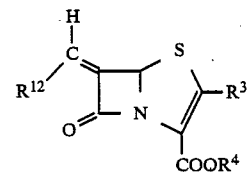

in which $R^3$, $R^4$ and $R^{12}$ are defined as above, with a compound represented by formula III

$R^5$—SH     III in which $R^5$ denotes an unsubstituted or substituted pyridyl, pyrazinyl, pyranidinyl, pyridazinyl, or benzthiazolyl group, in the presence of a base selected from the group consisting of an alkali metal carbonate and a substituted amine, said base being present in the reaction mixture in an amount within the range of from 0.01 to 2 moles per mole of the compound represented by formula II.

2. A process as claimed in claim 1, wherein $R^{12}$ is an unsubstituted or substituted furan, thiophene, pyrrole, pyrazole, imidazole, triazole, tetrazole, thiazole, isothiazole, oxazole, isoxazole, thiadiazole or oxadiazole ring.

3. A process as claimed in claim 1, wherein $R^{12}$ is an unsubstituted or substituted furan, oxazole, isoxazole, pyrazole or triazole ring.

4. A process as claimed in claim 1, wherein $R^{12}$ is an unsubstituted or substituted furyl, isothiazolyl, isoxazolyl, methylthiazolyl, methyloxazolyl, dimethyloxazolyl, methyl-1,2,3-thiadiazolyl, methyl-1,2,4-oxadiazolyl, N-methylpyrazolyl, N-methylimidazolyl, N-methyl-1,2,3-triazolyl, N-methyl-1,2,4-triazolyl, or N-methyltetrazolyl groups.

5. A process as claimed in claim 1, wherein $R^{12}$ is an unsubstituted or substituted pyridine, pyrazine, pyrimidine, pyridazine or triazine ring.

6. A process as claimed in claim 1, wherein $R^{12}$ is an unsubstituted or substituted 3-pyridyl, 4-pyridyl, methoxypyridyl, pyrazinyl, 4-pyrimidinyl, 3-pyridazininyl or dimethyltriazinyl group.

7. A process as claimed in claim 1, wherein $R^3$ is hydrogen.

8. A process as claimed in claim 1 wherein $R^4$ is a carboxyl protecting group.

9. A process as claimed in claim 1, wherein the compound of the general formula III is
2-mercapto-pyridine, 2-mercapto-pyrimidine,
2-mercapto-4,6-dimethyl-pyrimidine or
2-mercapto-benzthiazole.

10. A process as claimed in claim 1, wherein the base is potassium carbonate.

11. A process as claimed in claim 1 wherein the reaction is carried out in an aqueous or organic solvent or diluent.

12. A process as claimed in claim 1, for the preparation of one of the following compounds:
(5R) p-nitrobenzyl (Z)-6-(1-methyl-1,2,3-triazol-4-ylmethylene)penem-3-carboxylate, and
(5R) p-methoxybenzyl (Z)-6-(1-methyl-1,2,3-triazol-4-ylmethylene)penem-3-carboxylate.

* * * * *